(12) United States Patent
Molino et al.

(10) Patent No.: US 11,351,043 B1
(45) Date of Patent: Jun. 7, 2022

(54) PROSTHETIC ANKLE JOINT (71) Applicant: ST&G USA Corp., Placentia, CA (US)

(72) Inventors: Joseph L. Molino, Valley Cottage, NY (US); Michael Rebarber, Glen Rock, NJ (US)

(73) Assignee: ST&G USA CORP., Placentia, CA (US)

( * ) Notice: Subject to any disclaimer, the term of this patent is extended or adjusted under 35 U.S.C. 154(b) by 214 days.

(21) Appl. No.: 16/551,599

(22) Filed: Aug. 26, 2019

Related U.S. Application Data (60) Provisional application No. 62/722,495, filed on Aug. 24, 2018.

(51) Int. Cl.
| | |
|---|---|
| *A61F 2/66* | (2006.01) |
| *A61F 2/76* | (2006.01) |
| *A61F 2/50* | (2006.01) |
| *A61F 2/68* | (2006.01) |
| *A61F 2/30* | (2006.01) |

(52) U.S. Cl.
CPC ............ *A61F 2/6607* (2013.01); *A61F 2/76* (2013.01); *A61F 2/68* (2013.01); *A61F 2002/30433* (2013.01); *A61F 2002/5043* (2013.01); *A61F 2220/0033* (2013.01); *A61F 2220/0041* (2013.01)

(58) Field of Classification Search
CPC ............ A61F 2/6607; A61F 2/76; A61F 2002/30433; A61F 2/68; A61F 2002/5043; A61F 2220/0033; A61F 2220/0041
See application file for complete search history.

(56) References Cited

U.S. PATENT DOCUMENTS

| | | | | |
|---|---|---|---|---|
| 1,996,874 | A | * 4/1935 | Mascau | A61F 2/6607 623/49 |
| 5,728,175 | A | * 3/1998 | Rincoe | A61F 2/6607 623/49 |
| 6,187,052 | B1 | 2/2001 | Molino et al. | |
| 6,764,521 | B2 | 7/2004 | Molino et al. | |
| 7,914,587 | B2 | * 3/2011 | Archer | A61F 2/585 623/62 |
| 2011/0208322 | A1 | * 8/2011 | Rifkin | A61F 2/66 623/55 |

* cited by examiner

*Primary Examiner* — Yashita Sharma
*Assistant Examiner* — Melissa A Hoban
(74) *Attorney, Agent, or Firm* — Lawrence G. Fridman, Esq; Feigin & Fridman, LLC (57) ABSTRACT

A prosthetic ankle joint for a prosthetic foot attached to a base assembly. A linkage assembly provided between the base assembly and a torque bracket including an adapter unit disposed at top of the torque bracket to provide a connection to a lower tube-shaped clamp fitted over a pilon. The pilon extends upward to a second tube-shaped clamp connected to a lower portion of a socket receiving a residual limb of an amputee.

8 Claims, 12 Drawing Sheets

PROSTHETIC ANKLE JOINT

CROSS-REFERENCE TO RELATED APPLICATION

The present application claims priority of Provisional Patent Application Ser. No. 62/722,495 filed by the inventors on Aug. 24, 2018 the entire disclosure of this application is hereby incorporated by reference.

FIELD OF THE INVENTION

This invention relates in general to prosthetic devices, and more particularly to prosthetic ankle joints.

BACKGROUND OF THE INVENTION

Each foot and ankle during walking travel through stance and swing phases of a gate cycle. In the stance phase, the foot is in contact with the ground and the weight of a person is supported on the foot. In the swing phase, the foot is off the ground as the entire leg and foot move from a posterior position to an anterior position with respect to a center of gravity of the person. The stance phase begins just after completion of the swing phase and commences with a heel strike wherein the foot is lowered to the ground as the body moves forward from a position posterior to the person's center of gravity. Immediately after heel strike, the foot moves from a dorsiflexed position, wherein the toes of the foot are pointed upwards, to a plantarflexed position wherein the bottom of the foot or shoe is flat on the walking surface, which provides greater stability as the entire weight of the person is shifted over the foot in contact with the ground. The swing phase commences just after heel strike of the other foot. During the swing phase, the foot is again in the dorsiflexed position as the foot leaves the walking surface and the foot and leg swing forward in preparation for the stance phase. Dorsiflexion is essential for normal human locomotion, since the toes must be dorsiflexed in order to clear the floor. If the foot were not dorsiflexed during the swing phase, it would most likely catch on the walking surface and cause the person to stumble and fall, leading to potentially serious injury.

For the purposes of this disclosure, the term medial refers to the person's center of gravity, whereas the medial movement is the sidewise, inward movement toward the center of gravity. The term lateral motion is defined herein as the sidewise outward movement from the center of gravity. In the neutral or medial position, the interior and exterior parts of the foot are positioned substantially horizontally. Two inclined positions of the human foot in both directions from the vertical are defined herein as inversion and aversion. The inversion or inverted position occurs when an exterior part of the foot is sloped downwardly, while an interior part of the foot is directed upwardly. In the opposite respect, the eversion or inverted position of the foot occurs when the exterior part of the foot is directed upwardly and the interior part of the foot slopes downwardly. The inclination of the human foot in the inverted and everted positions ranges between 0. degree and 15. degree to the horizontal plane.

There are currently available prosthetic ankle joints which are designed to assist a user during walking or travel through stance and swing phases of a gait cycle. An example of such modern prosthetic ankle joint is provided by the inventors' own U.S. Pat. Nos. 6,187,052 and 6,764,521 which are incorporated by reference by the present application in their entirety.

SUMMARY OF THE INVENTION

For purposes of this description, the terms "upper," "bottom," "right," "left," "front," "vertical," "horizontal," and derivatives thereof shall relate to the invention as oriented in figures of the drawing. It is to be understood that the terms inner, outer, upper, lower, vertical, horizontal, upright, anterior, posterior, and their respective derivatives as used throughout the specification refer to relative, rather than absolute positions or orientations.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

One aspect of the invention provides a prosthetic ankle joint consisting a movement mechanism having a base and a base member cooperating with each other. An elongated opening extends through the base member formed with a lower base portion having an open bottom area. The base is defined by at least anterior and posterior walls, with each anterior and posterior walls being formed having an opening. A substantially hollow receiving inner cavity extends inwardly within the lower base portion from the open bottom area. The base member is movably positioned within the receiving inner cavity and is movably secured within the cavity by a shaft rotatably supported within said elongated openings of the base member. Rotation of the shaft is resulted in a longitudinal motion of the base member within the receiving inner cavity.

Another aspect of the invention provides a prosthetic ankle joint having a vacuum assembly associated with a socket for receiving a residual limb of human body. The prosthetic ankle joint includes a base, a linkage assembly between the base and a torque bracket having an adapter unit connected to a socket. The vacuum assembly comprises the adapter associated with a torque bracket, a piston traveling longitudinally inside the cylinder provided at the adapter, with the cylinder defining a vacuum chamber. A link connects a top area of the linkage assembly to the piston. In a dorsiflexed position the link pulls the piston downward to create a hollow space within the vacuum chamber causing formation of a vacuum. The vacuum delivered to a space between a socket interior and the residual limb to create suction for holding the socket on the residual limb.

A further aspect of the invention provides a prosthetic ankle joint having a dorsiflection mechanism for achieving active dorsiflexion. The prosthetic ankle joint includes a torque bracket pivotably connected to a base assembly by a linkage assembly. The torque bracket includes an upper arm with a lower arm extending downwardly from the upper arm. The linkage assembly having a top portion and two spaced from each other side walls extending from the top wall. The dorsiflection mechanism is disposed at an interface of an interior of the torque bracket, the lower arm and the linkage assembly. An adjustment pin extending between an inner portion and an outer portion thereof. The mechanism also includes first and second active dorsiflexion assemblies separated by the adjustment pin. Each dorsiflexion assembly comprises a channel oriented transversely to the adjustment pin. The channels house two inner active dorsiflexion adjustment balls engaging the inner portion of the pin, two adjustment biasing elements provided to engage the respective inner balls and outer balls, each outer ball engages respective detents formed in the side walls of the top portion.

The description of the present invention has been presented for purposes of illustration and description but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

BRIEF DESCRIPTION OF THE DRAWINGS

Referring now to the drawings which are provided to illustrate and not to limit the invention, wherein.

DETAILED DESCRIPTION OF THE INVENTION

We are referring to inventors' own U.S. Pat. No. 6,187,052 which is incorporated herewith as a reference in its entirely. The features of the present invention relate to the base mounting foot and adjustment of the foot in relation to the ankle. More specifically, the essential features of the invention enable a user of a prosthetic device to incrementally increase the distance from the heel of the foot attached to the ankle to the actual ankle itself. In U.S. Pat. No. 6,187,052 this task was accomplished utilizing a sliding mechanism consisting of a dovetail on the base in contact with the superstructure above the base to slidably adjust utilizing the dovetail and utilizing an adjustment screw to increase the distance between the superstructure and the mounting foot piece to increase the distance between the heel. Thus, the fulcrum was increased to be able to adjust the weight needed to activate the ankle. By moving the distance further from the heel, the force to activate the ankle is reduced and less force is applied to deform a urethane bumper enclosed within the superstructure of the ankle. In U.S. Pat. No. 6,764,521 the urethane bumper is used to mimic a co-contraction of the anterior tibialis muscle group, therefore slowing down the decent of the front of the foot to eliminate foot slap on ground contact and to decelerate the anterior distal portion of the foot. In this manner the foot does not physically slap the ground but will do that in a gentle controlled fashion. This adjustment is essential because the device is applicable to a wide range of patient weights and leg lengths that affects the rate at which the device allows the foot to decent to ground contact during the plantarflexion of the foot. By decreasing the distance between the heel and the movable portions of the ankle it would require more force. Therefore, to accommodate needs of very heavy patient or very long-legged patients during the use of this prosthetic ankle joint, it will be necessary to adjust the ankle joint more rearward or posterior to center of rotation of the ankle. This sometimes makes it more difficult to achieve the total plantar flexion. However, if a patient is lighter and needed less weight to activate the ankle the ankle is moved more interior. This requires less force to activate the ankle to bring it to plantarflexion.

Further engineering investigations uncovered the need to revise the prior art sliding mechanism consisting of a dovetail on the base in contact with the superstructure above the base. This is because the forces necessary to isolate the motion of the dovetail contribute to unwanted stress on the web of dovetail.

Figure 1:
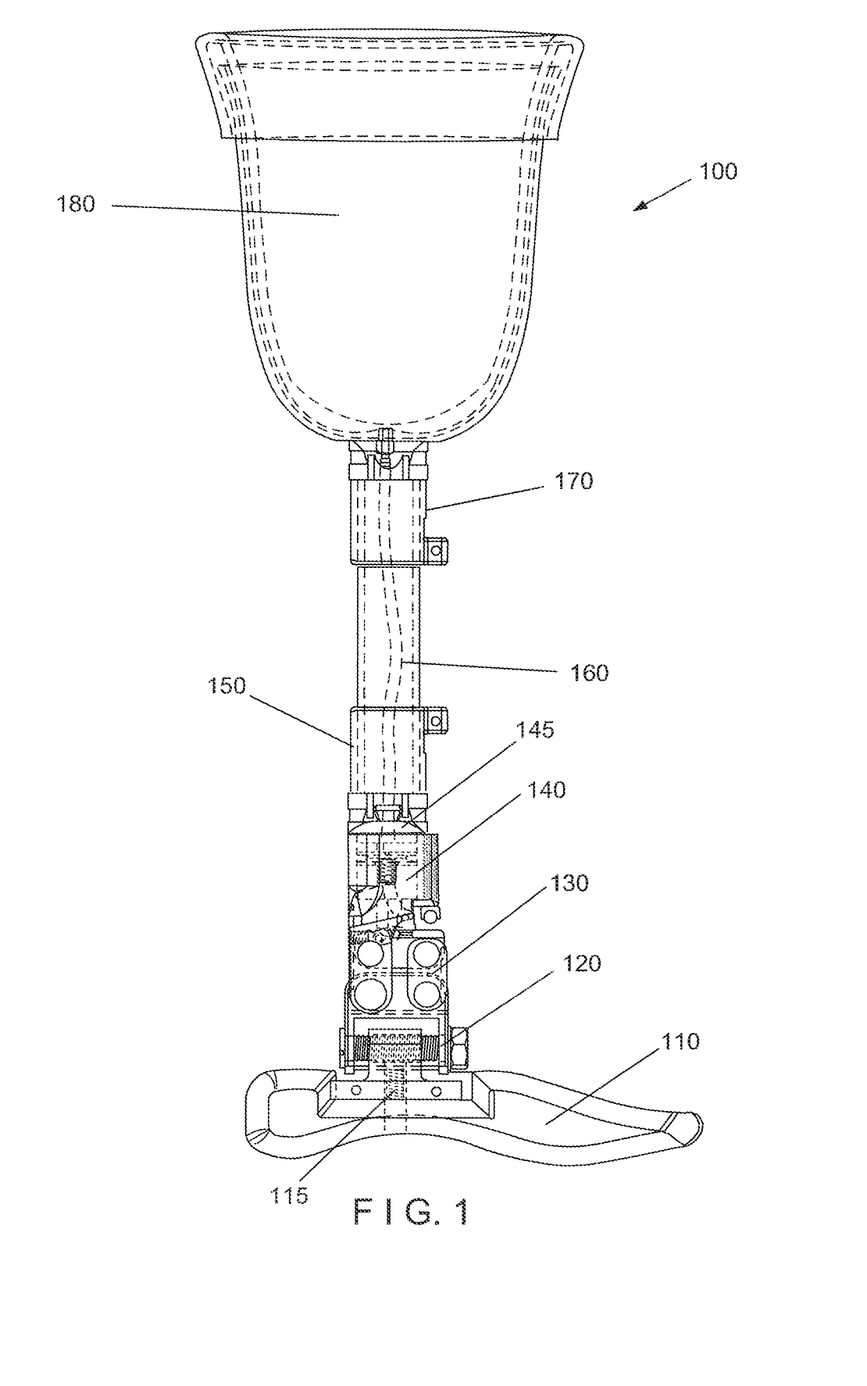
FIG. 1 is a general view illustrating a chain of componentry of the prosthetic foot of the invention.
Figure 1A:
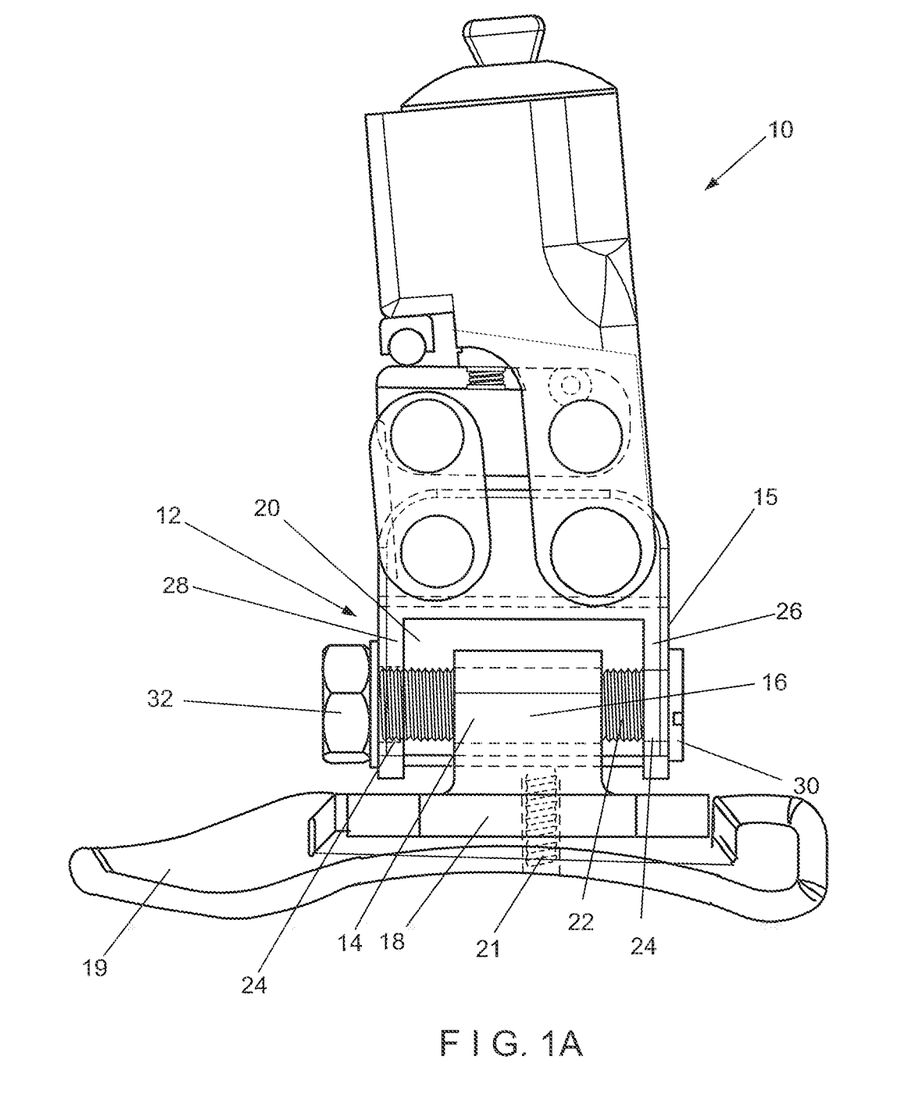
FIG. 1A is an elevational view showing the first embodiment of the invention.
Figure 2:
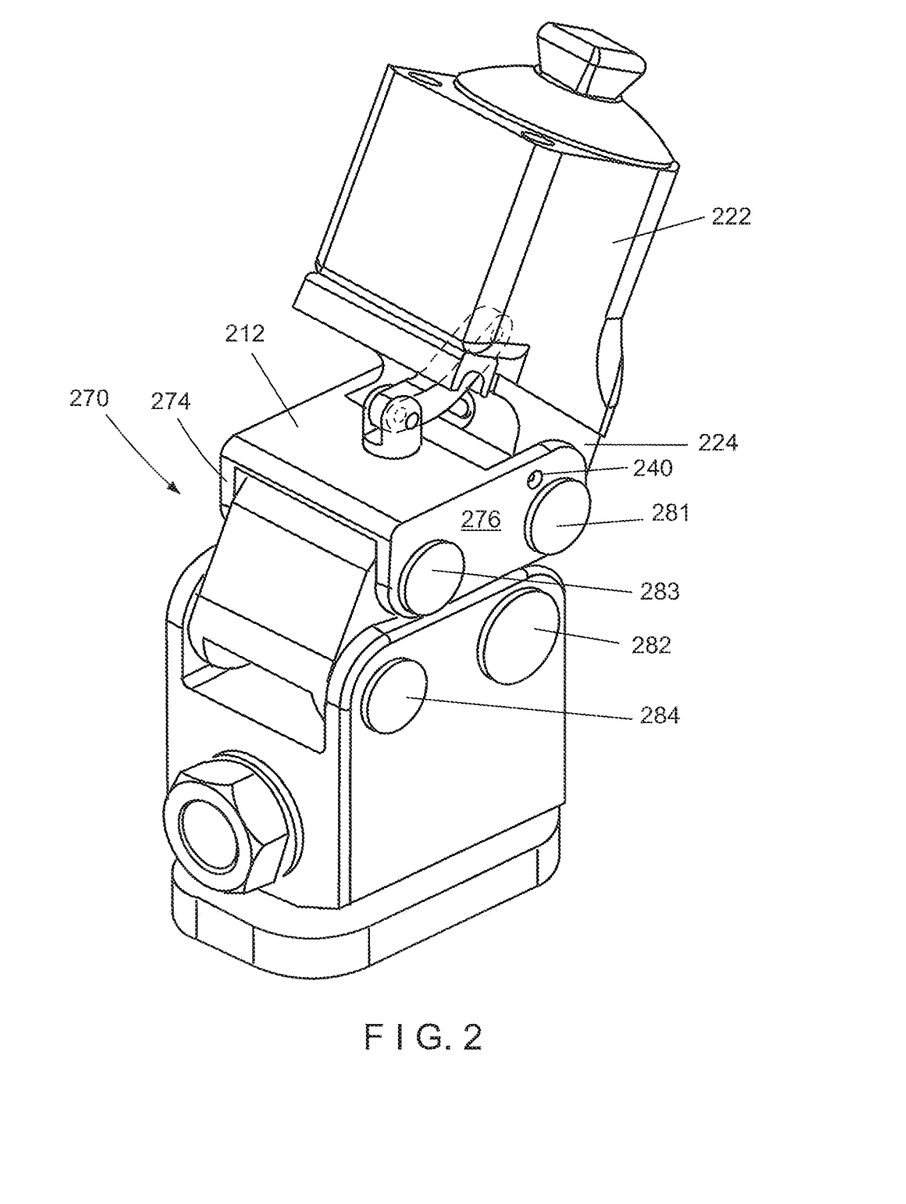
FIG. 2 is a semi-perspective view of the second embodiment of the invention providing a dorsiflexion mechanism.
Figure 2A:
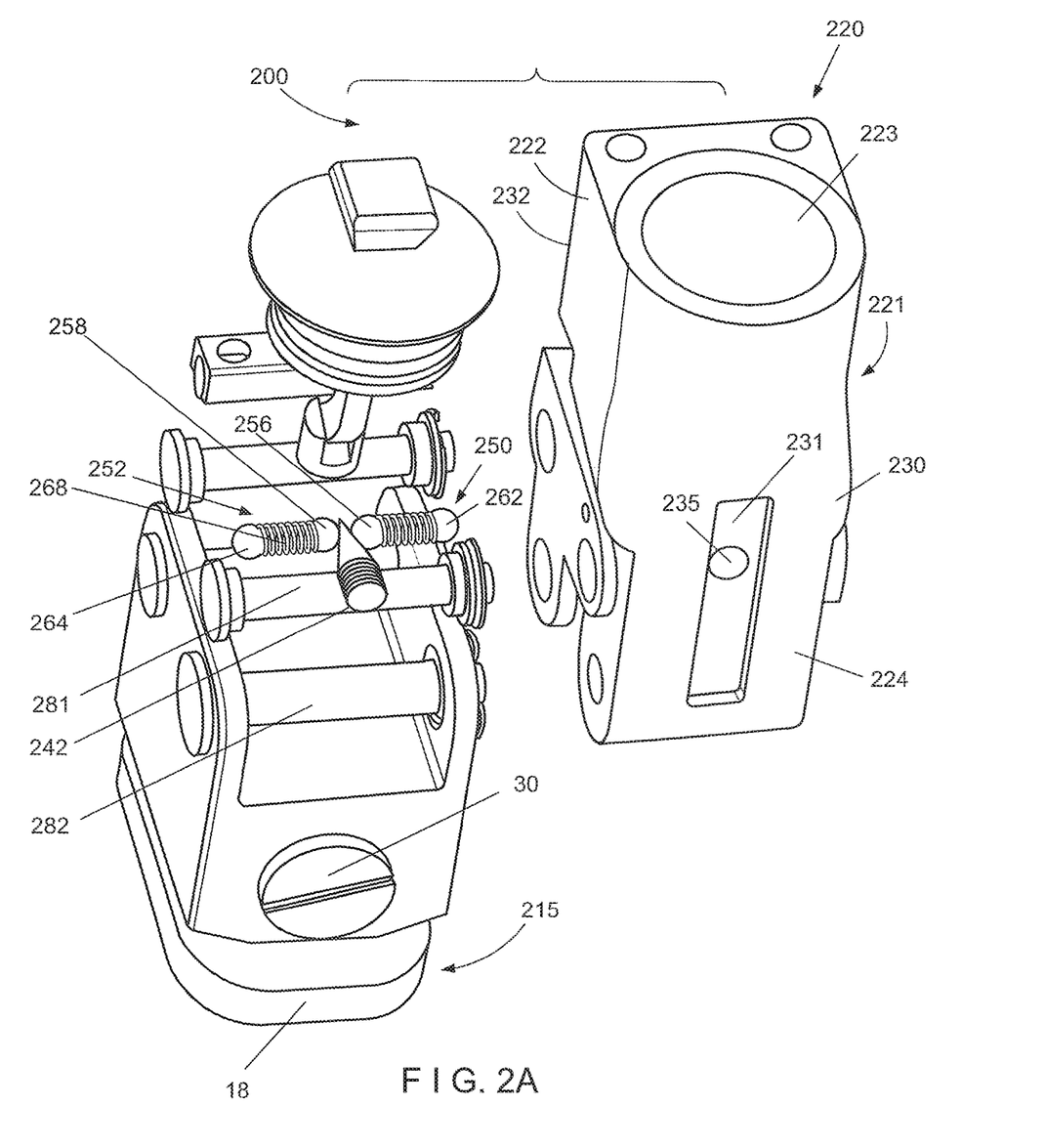
FIG. 2A is another view of the second embodiment of the invention showing componentry of the dorsiflexion mechanism.
Figure 3:
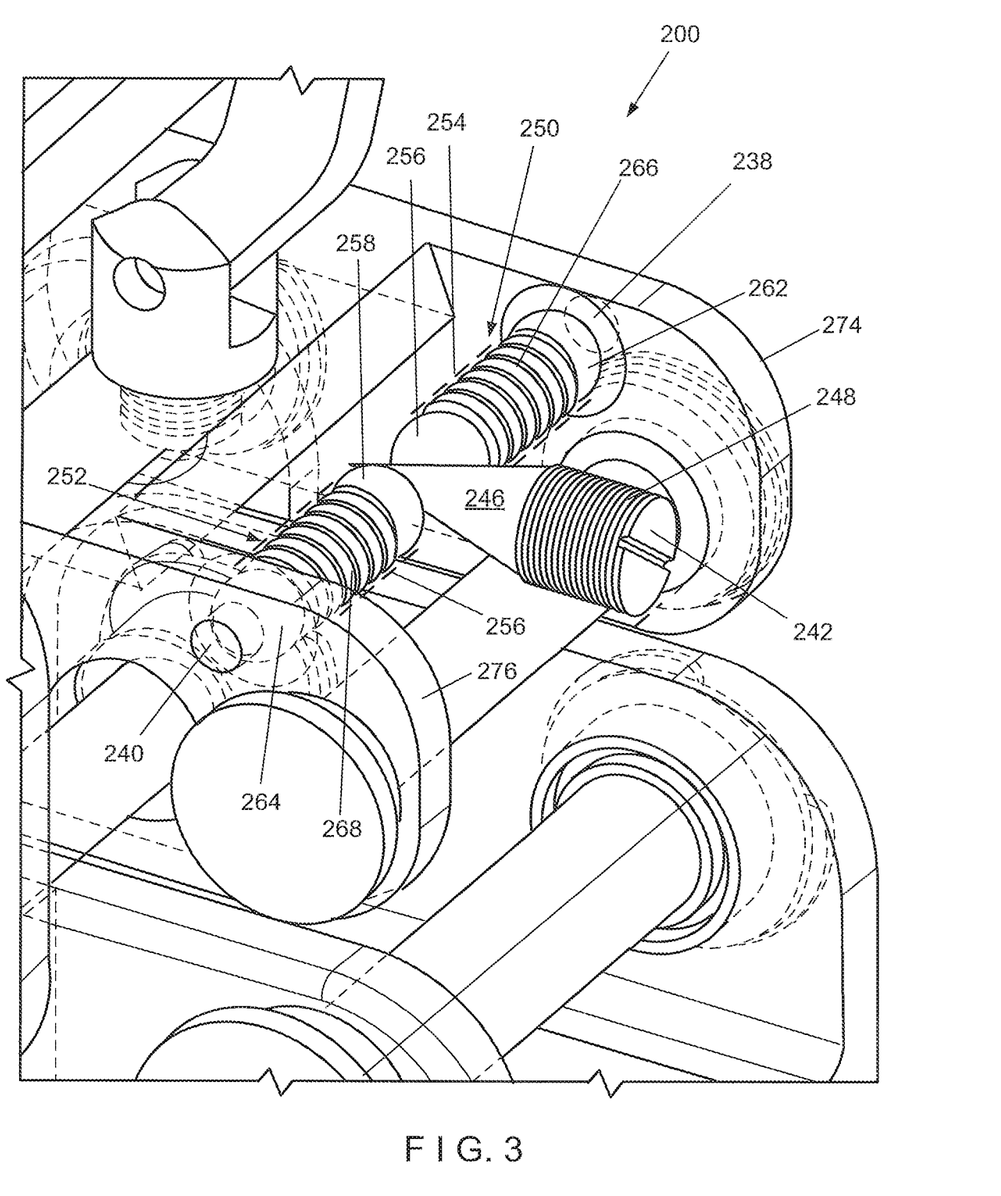
FIG. 3 is an enlarged partial view showing the componentry of the dorsiflexion mechanism.
Figure 3A:
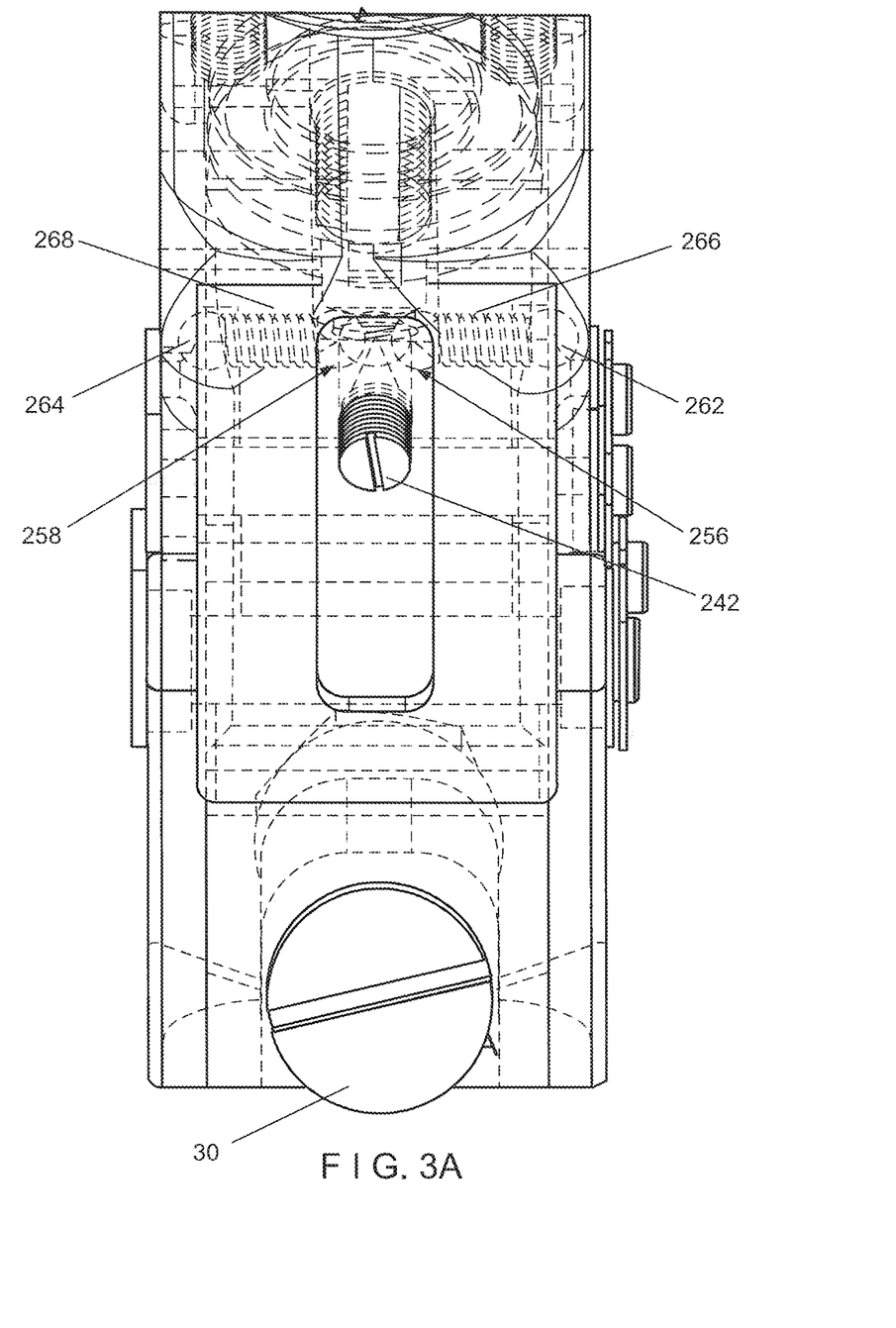
FIG. 3A an elevational view showing external aspects of dorsiflexion mechanism.

Referring now to the drawings, and FIG. 1 in particular which illustrates a chain of componentry of the prosthetic foot 100 of the invention. A foot 110 is fixedly attached by means of a fastener/bolt 115 to a base assembly 120 of the ankle. A linkage assembly 130 is provided between the base assembly and a torque bracket 140 including an adapter unit 145. The adapter unit is disposed at the top of the torque bracket 140 to provide a connection to a first or lower tube-shaped clamp 150 that is compression fitted over a pilon 160. In one of the embodiments the assembly also includes a compression fastener which passes through a tube at an upper area of the first tube-shaped clamp 150. The pilon 160 and the first tube clamp 150 are fixedly attached to each other and the pilon extends upward to a second tube tube-shaped clamp 170, which is in turn connected to a lower portion of the socket 180. The socket 180 ends a chain of componentry to complete composition of the prosthetic foot 100 of the invention.

Description of the First Embodiment

In the embodiment of FIG. 1 the prosthetic ankle joint 10 comprises a base assembly including the movement mechanism 12 with a base 15 (inversion-eversion component) and a base member 16 with a bottom portion 18 connected to a foot 19 by a fastener 21. The base 15 extends between its proximal end and a distal end and is formed with a lower base portion. The base 15 is defined by an anterior wall 26 and posterior wall 28 which are interconnected by side wall(s). A substantially hollow receiving inner cavity 20 extends inwardly within the lower base portion from an open end. The base member 16 associated with the foot 19 is movably positioned within the receiving inner cavity 20. A movement mechanism 12 which is provided to migrate the base member 16 and the foot 19 either forward or aft forms an essential aspect of this embodiment.

The movement mechanism 12 of the prosthetic ankle joint 10 illustrated in FIG. 1 comprises an elongated threaded opening 14 extending through the entire length of the upper part of the base member 16. The foot 19 and the base member 16,18 are movably secured within the cavity 20 by a threaded shaft 22. The shaft is rotatably supported within the respective openings 24 in the anterior wall 26 and the posterior wall 28 and threadably engages the elongated opening 14. When the threaded shaft 22 is rotated, the head 30 of the shaft pushes against the walls 26 and 28, whereas the threads of the shaft 22 engage the treads of the elongated opening 14.

As the shaft 22 is turned in one direction, through the threaded engagement the base member 16 and the foot 19 are moved in the anterior direction. When the shaft 22 is rotated in another direction it causes the base member and the foot to move in the posterior direction. Once the desired position and action of the ankle is achieved, the shaft 22 is then locked by the lock fastener 32 or a nut. In this manner, the base member 16 encompassing the foot 19 is not allowed to migrate either forward or aft anymore.

To adjust the ankle joint utilizing the movement mechanism 12 position of the foot 19 is longitudinally adjusted within the cavity 20 by turning the adjustment shaft 22. When the threaded adjustment shaft is rotated, the threads of the elongated opening 14 are engaged, causing the base member 16 and the foot 19 to move either forward or backward, thus increasing or decreasing the length between the heel contact area of the foot and the center of rotation of the ankle.

Description of the Second Embodiment

In the prior art (U.S. Pat. No. 6,187,052) the active dorsiflexion is achieved by utilizing characteristics of the resilient block or a bumper, which upon deformation slowly returns to its original shape, and to bring the ankle joint back to its original resting point. By slowly returning to its original shape the resilient block provides a few degrees of dorsiflexion to enable ground clearings during swing phase.

It will be discussed below that the above-discussed issues have been addressed in the embodiment of the present invention illustrated in FIGS. 2, 2A, 3 and 3A, which illustrate a prosthetic ankle joint having 3-5-degree anterior lean of the tube clamp. This position allows the ball detent to engage with the detent in the horizontal leg holding the foot in a temporary dorsiflexed position, so as to allow adequate toe clearance during swing phase. This is a safety feature provided to eliminate toe catching with the walking surface.

Referring now to FIGS. 2, 2A, 3 and 3A which illustrate a novel dorsiflection mechanism 200 of the invention provided to assure that active dorsiflexion is achieved by the prosthetic ankle joint of the invention. The torque bracket 220 is pivotably connected to the base assembly by a linkage assembly 270. The torque bracket 220 with the housing 221 is generally inverse L-shaped in configuration and includes an upper arm 222 that extends in a generally horizontal direction a lower depending arm 224 that extends downwardly from the upper arm 220. A top opening 223 is formed at a top area of the upper arm providing access to an interior of the housing 221.

The linkage assembly 270 comprises a generally U-shaped top portion 272, which is formed with two spaced from each other side walls 274 and 276 extending from a substantially flat upper wall 278. Multiple pins 281,282,283 and 284 are provided for pivotal connection between the elements of the assembly 270 and other elements of the invention. For example, pins 281 and 282 provide pivotal connection between the lower arm 224, the top portion 272 and the base assembly.

The dorsiflection mechanism 200 is disposed at an interface of an interior of a housing 221 of a torque bracket 220, the lower depending arm 224 and the linkage assembly 270.

The housing 221 is formed by a posterior wall 230 and an anterior wall 232 interconnected side walls. In U-shaped top portion 272 each side wall 274, 276 is formed with detents/opening 238,240. The posterior wall 230 is formed with a recess 231 having a threaded aperture 235. The dorsiflexion mechanism 200 comprises an adjustment pin 242 which extends between an inner portion 246 having a conical configuration and an outer portion 248. The outer portion is formed with the threads adapted for engagement with the treads of the aperture 235. The mechanism 200 also includes first 250 and second 252 active dorsiflexion assemblies separated by the adjustment pin 242. Each dorsiflexion assembly 250,252 comprises a channel 254,256 oriented transversely or perpendicular oriented to a longitudinal axis of the adjustment pin 242. The channels house two inner active dorsiflexion adjustment balls 258 and 256 that engage the inner portion 246 of the pin 242. The channels 254,256 also house two adjustment biasing elements or springs 266,268 provided to engage the respective inner ball 258, 256 and outer balls 262, 264. Each outer ball also engages the respective detents 238,240 that are formed in the side walls 274 and 276 of the top portion 272.

When the pin 242 is rotated, in one direction, through the engagement of the threads of the outer portion 248 with the threads of the aperture 235, it is adjusted in the inward direction. In this manner the inner conical portion 246 exerts increased pressure on the inner ball 256,258 to allow the outer balls 262,264 to be forcibly disposed within the detents 238,240 in the side walls 274 and 276. In this manner, a fixed position is maintained when the foot is in a dorsiflexed position allowing a momentary stationary position, wherein the toes are pointed upward in the swing phase.

When a patient goes into a position loading the toe, the torque bracket 220 is in a less than vertical position forward between 3 and 15 degrees of interior tilt of the limb in relation to the ground. At this point, the pressure exerted by the inner conical portion 246 of the pin 242 is applied on the inner balls 256,258 pushing the springs 266,268 and ultimately pushing the outer detent balls 262,264, so as to allow the outer balls to secularly migrate into the detents 238,240. This ensures that a dorsiflexed relationship exists between the foot and the leg and assures a toe up position. Thus, the patient can clear the ground during swing phase without engaging his toe. At the end of the swing phase, the next phase is the heel strike.

When the heel hits the ground, the springs 266,268 pressure on the outer detent balls 262,264 (to be retained in the detents 238,240) is overcome by the force exerted by the heel to force the prosthetic ankle joint of the invention into a plantarflexed position. There is more force exerted by the heel, therefore it overcomes the force applied by the springs pushing the outer detent balls 262,264 into the detents 238,240. Therefore, the outer detent balls 262,264 are allowed to climb up the slope of the respective detents and to move freely to allow full plantar flexure.

The above-discussed doresiflection mechanism 200 is provided to adjust the force necessary to engage the outer detent balls 262,264 into the respective detents 238,240 with the active dorsiflexion adjustment pin 242 being adjusted in or out. This changes the force exerted on the inner active dorsiflexion adjustment balls 255,258 and springs 266,268 to increase or decrease the force required for the outer detent balls 262,264 to firmly engage in the respective detents 238,240. This arrangement allows the fine adjustment of the force necessary to hold the foot in a slightly dorsiflexed position for safe swing phase and to eliminate toe catching. When the foot advances to the heel strike, the force of this action will overcome the spring tension holding the outer detent balls 262,264 in the respective detents and disengage the active dorsiflexion until the heel off when it will reengage for the swing phase.

When the adjustment pin 242 is turned in one direction it provides more pressure on the inner active dorsiflexion adjustment balls 256,258 which in turn increases the pressure on the springs 266,268, which in turn increases the pressure on the outer detent balls 262,264. As a result, greater force is applied on the outer detent balls to fall into the respective detents. The outer detent balls 262,264 are locked into the detents 238,240, while the foot is in dorsiflexed position. When the gate cycle is advanced through swing phase, it provides increase in the dorsiflexion angle in relation to the leg. Therefore, a toe up position is provided. In this manner, the swing phase does not allow for toe catching and/or contribute to any stumbling that may take place because the foot has contacted the walking surface. When that phase of the gate cycle is complete, the patient then goes into heel strike. The force of heel strike will overcome the springs 266, 268 tension forcing the outer balls 262,264 into the detents 238,240 allowing the ankle to release its captive state holding the foot in upright position and allowing a smooth transition via the slope in the detent area on the horizontal leg. This allows the balls to gently retract inward towards the center of the channels 250,252 and provides a smooth transition for toe up position. The latter is necessary during swing phase to improve the ability of the device to slowly plantarflex and get the foot flat on the floor from heel strike.

Description of the Third Embodiment

Referring now to FIGS. 4-7 illustrating a third embodiment related to a vacuum generating mechanism of the invention. An essential aspect of this embodiment of the invention is based on the principal that in operation of the above-knee prosthetic legs, addition vacuum aids in securing the residual limb within interior of the socket. More specifically, a negative pressure generated by the device of the invention between the socket interior and the inserted residual limb is resulted in suction, which retains the limb in substantial contact with the interior surface of the socket. In the invention this is facilitated by providing a liner with a silicon interlining and a cloth outer lining over the residual limb. In this manner, as vacuum is exerted to the interior of the socket, it acts on the material side of the liner. Therefore, the generated vacuum pressing the limb against the socket provides substantially improved contact therebetween. It will be discussed below that vacuum formed during operation of the device of the invention is developed during the plantar flexure phase of the ankle unit motion.

Figure 4:
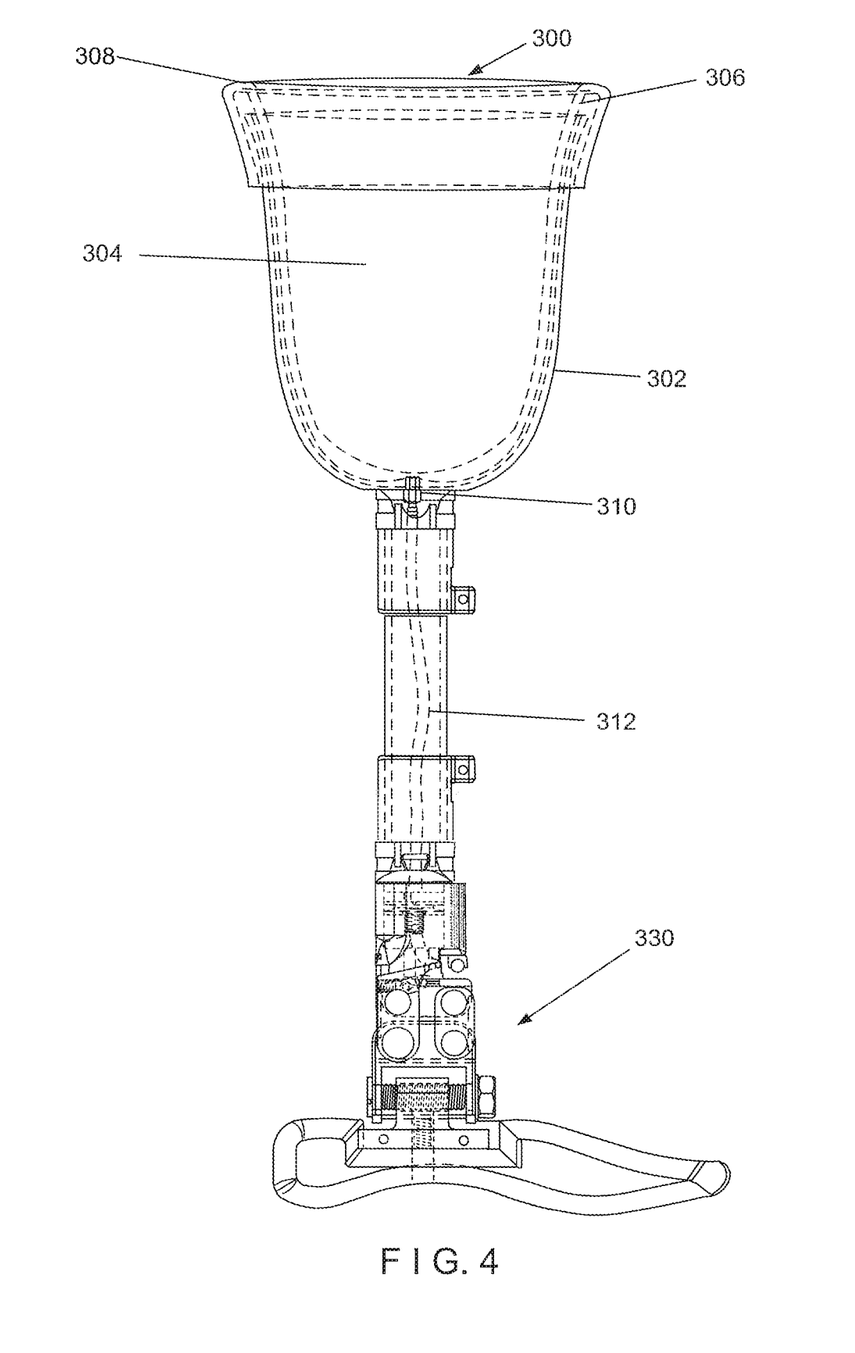
FIG. 4 is an elevational view showing a vacuum generating mechanism of another embodiment of the invention.
Figure 5:
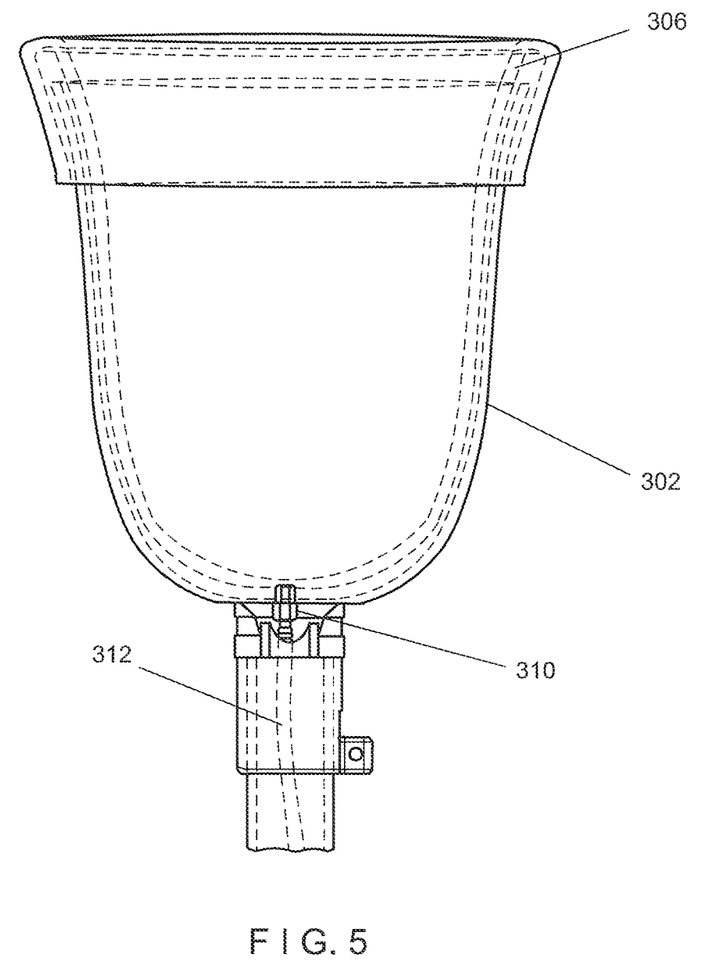
FIG. 5 is a partial elevational view showing a socket associated with the vacuum generating mechanism.

With reference first to FIGS. 4 and 5, an above-knee prosthetic leg is designated generally by the numeral 300 and includes a socket 302 of a suitable material, such as plastic for example, for receiving a residual limb of an amputee. The liner 306 with a silicon interlining and a cloth outer lining is provided in the socket interior 304 over the residual limb. The socket 302 is coupled by a conventional means to remaining parts of the prosthetic leg. A check valve 310 with an adjustable vacuum regulation bleed arrangement is installed between a vacuum delivery tube 312 (or at any other suitable location), connected to the vacuum chamber, and the socket interior 304 to regulate the amount of vacuum allowed. An exterior edge/lip 308 at the top of the socket 302 provides an additional seal to the vacuum created within the socket interior 304 preventing escape of the vacuum to the atmosphere.

Figure 6:
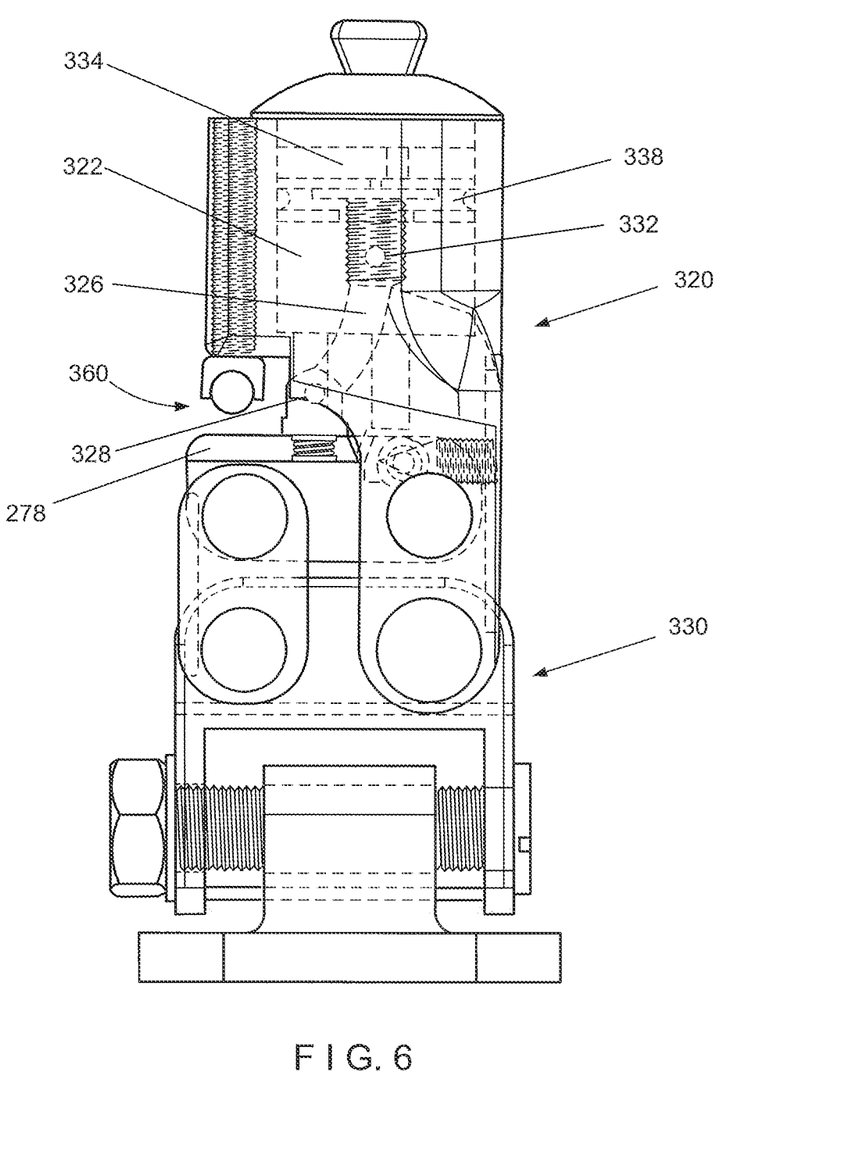
FIG. 6 is an elevational view showing a cylinder-piston assembly of the vacuum generating mechanism.
Figure 7:
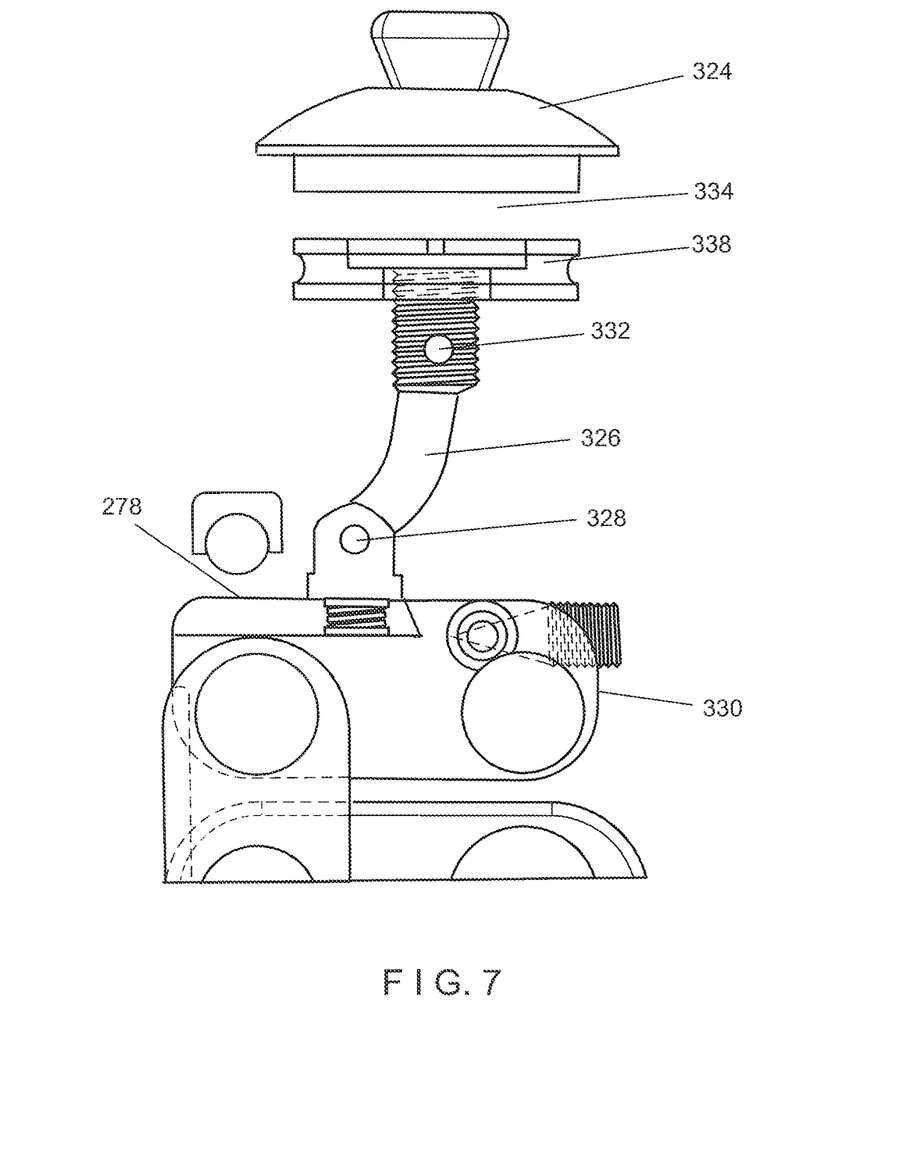
FIG. 7 is an enlarged view a cylinder-piston assembly.

Referring now to FIGS. 6 and 7, a vacuum mechanism 320 comprises a cylinder 322 is provided in the interior of the housing 221 between a pyramid cup/adapter 224 and an ankle joint 330. A link 326 connects a base pin 328, provided at the upper wall 278 of the top portion 272 in the ankle joint 330, to the piston pin 332 disposed in the central area of the piston 338. The piston 338 is allowed to travel longitudinally inside the cylinder 322 connected to the bottom portion of the vacuum tube 312 (see FIG. 4). In one embodiment the piston 338 can be provided with multiple oval rings to prevent escape of the vacuum.

FIG. 6 illustrates the prosthetic ankle joint 330, forming a part of the prosthetic leg, in a dorsiflexed position. As the link 326 pulls the piston 338 downward, it creates a hollow space within the vacuum chamber 334 of the cylinder 322. This causes formation of a vacuum, which is delivered through the tube 312 to the space between the socket interior 304 and the residual limb. The vacuum creates suction to assist in holding the socket firmly on the residual limb. In the invention the generated vacuum is also used to regulate the speed of the operation of the ankle joint.

As the leg goes through the motion of plantar-flexing, the base pin 328 associated with the upper wall 278 of the top portion 272 of the prosthetic ankle joint 330 and the link 326 connected thereto are pulled downward. In view of the connection between the link 326 and the piston pin 332 (attached to the piston center), the entire piston assembly is pulled downward creating an increased hollow space within the chamber 334 of the cylinder 330 creating vacuum. The vacuum is allowed to be transferred through the vacuum delivery tube 312 and the check valve 310 into the socket interior 304. The adjustable check/bleeder valve 310 prevents formation of the excessive vacuum within the socket interior which may cause undesirable edema on the patient's limb. By means of the check/bleeder valve 310, the vacuum can be adjusted to approximately 12 to 15, 16 inches of mercury. This ensures adequate vacuum to retain the limb firmly against the socket interior 304 utilizing negative pressure. This secures the limb in contact with the socket interior, so as to prevent disengagement from the socket.

As the prosthetic leg is moved, the ankle joint 330 cycles from the planta-flexion through the gate cycle to mid stands, to heel off and again the cycle begins at the heel strike. At the heel strike, the piston 338 is allowed to move downwardly within the cylinder 322 creating additional vacuum directed to the socket interior. In the invention, as the person walks, a vacuum is continually generated and applied to securely retain the residual limb within the socket 302. By means of the valve 310, the excessive vacuum is bled off from the socket interior 304. By the check valve 310, which can be spring-loaded, the access vacuum is releases to ensure that only the required amount of vacuum remains in the socket interior 304.

Another essential aspect of this embodiment of the invention relates to the use of the device to regulate the speed of the decent of the ankle joint 330 from planta-flexed to a neutral position. In this manner, the invention not only generates the vacuum to secure the limb within the socket interior 304 but is also used as a regulatory device to regulate the speed and operation of the ankle joint emulation to the patient walking. This makes a very smooth transition from plantar-flexion to foot flat, to toe loading, to heel off, and to the swing phase. In the invention such transition can be timed via the valve to ensure smooth operation of the ankle during the gate cycle.

Description of the Forth Embodiment

As previously discussed regarding the embodiment FIGS. 6 and 7, the vacuum mechanism 320 comprises the cylinder 322 and the piston 338 provided below the pyramid adapter 324 and disposed inside the upper portion of the torque bracket associated with the ankle joint 230.

Figure 8:
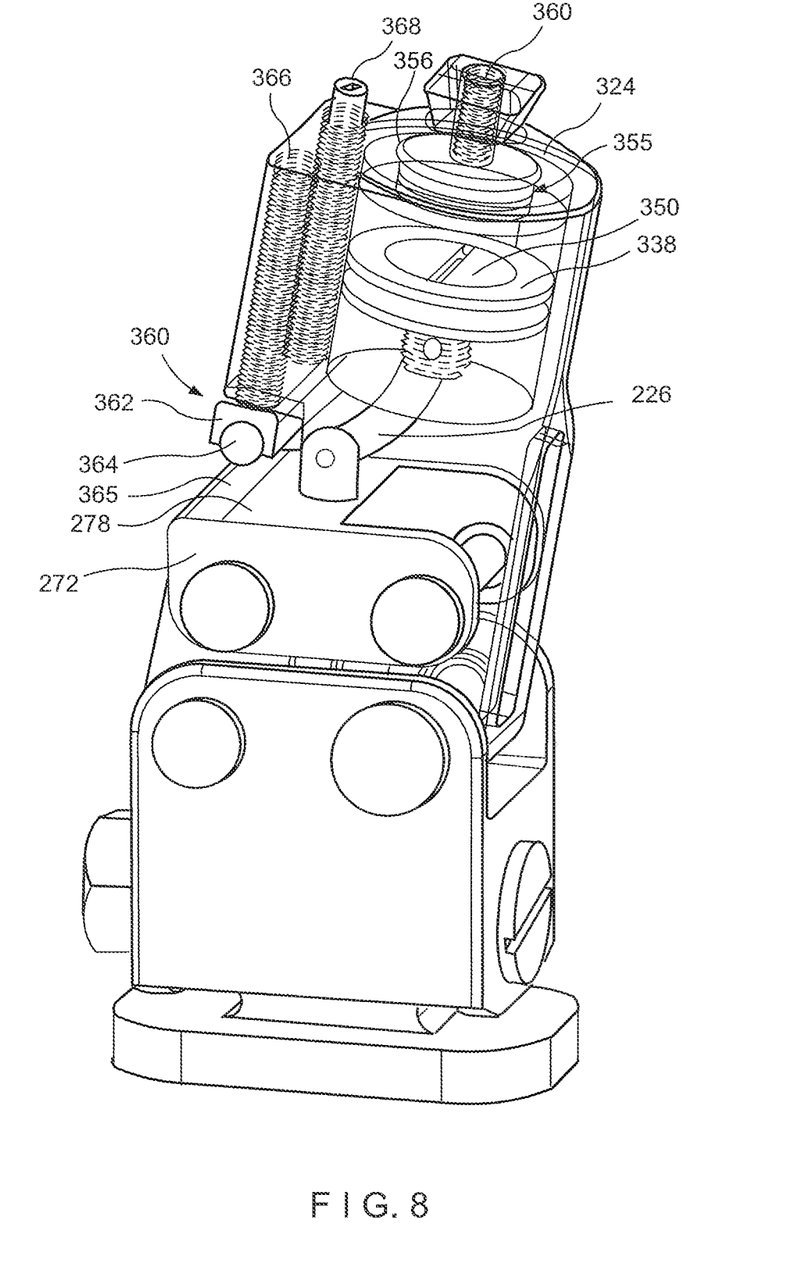
FIG. 8 is a semi-perspective view of an alternate embodiment of a dorsiflexion mechanism.

In the embodiment of FIG. 8 a central area of a top portion of the piston 338 is provide with a magnetic plate 350. A lower region of the pyramid adapter 324 is formed with a cavity 355 configured to adjustably receive a magnetic insert 356.

An adjustable connection between the cavity 355 and the magnetic insert 356 is provided. In the embodiment FIG. 8 such adjustable connection is in the form of internal threads provided in the cavity interior and external threads on the magnetic insert peripheral exterior. Thus, the threaded magnetic insert 356 is rotationally adjusted in upward or downward directions within the threaded cavity 355 of the pyramid adapter. In this manner, a controllable magnetic connection is established between the magnetic insert and the magnetic center plate that is attached to the vacuum piston 338 of the ankle. It should be clear to a person of ordinary skill in the art that any conventional arrangement facilitating controllable movement and adjustment of the magnetic insert 356 relative to the cavity 355 is contemplated.

As illustrated in FIG. 8 a stop and bumper assembly 360 is provided at the anterior bottom portion of the torque clamp, with a holder 362 containing a bumper 364 extending from the lower region of the assembly. The assembly is formed with at least one or multiple longitudinal apertures 366 passing through an anterior-lateral and medial side of the torque clamp. The apertures 366 are configured to adjustably receive supporting members 368 associated with the bumper holder of the bumper assembly. The longitudinal apertures 366 are formed with internal threads and the supporting members 368 are formed with cooperating external threads. Thus, upon rotation of the supporting members 368 within the apertures 366 in one direction the stop and bumper assembly 360 is moved closer to a stop plate 365 provided at the upper wall 278 of the top portion 272 of the linkage. This motion ultimately regulates the amount of dorsiflexion that the foot is allowed to rest at. In similar fashion, upon rotation in the opposite direction the stop and bumper assembly 360 moves away from the stop plate 365.

The pyramid magnetic insert 356 is rotationally adjustable within the pyramid adapter 324 to increase or decrease the distance between the magnetic insert and the magnetic center plate 350, to allow the adjustment of the angle of active dorsiflexion. This arrangement combined with the adjustable stop and bumper assembly 360 prevents excessive forces to be applied on the magnetic center plate 350 by the magnetic insert 356. In the invention the majority of forces causing anterior motion of the bottom of the torque clamp in relation to body of the prosthetic ankle are minimized by the adjustable stop and bumper assembly 360 which contact the stop plate 365. The excessive forces should be prevented from being transmitted to the magnetic center plate 350 and adjustable magnetic insert 356. The only forces allowed are the forces exerted by the attraction of the magnets to maintain a toe up position.

There is maximal distance between the magnetic center plate 350 and the magnetic insert 356. As the foot rotates to midstance, the distance between magnetic center plate 350 and magnetic insert 356 is decreased. When the optimum angle of active dorsiflexion is achieved on toe loading, the magnetic forces on the magnetic center plate 350 in relation to the magnetic forces of the magnetic insert 356 are activated. Therefore, the magnetic insert 356 is attracting the magnetic center plate 355 and a toe up position of the leg in relation to the foot is maintained.

The embodiment of FIG. 8 provides an alternate arrangement and method of maintaining the toe in the dorsiflexed position. In the previously discussed embodiment of FIGS. 2 2A,3 and 3A the inner and outer balls typically made from hardened materials are utilized to enact a dorsiflexed position of the foot. Although this arrangement provides good reliability, the hardened materials are not always readily available. The embodiment of FIG. 8 provides an alternate way of controlling the active dorsiflexion without use of the hardened materials, and therefore is somewhat simpler and less expensive.

Description of the Fifth Embodiment

Figure 9:
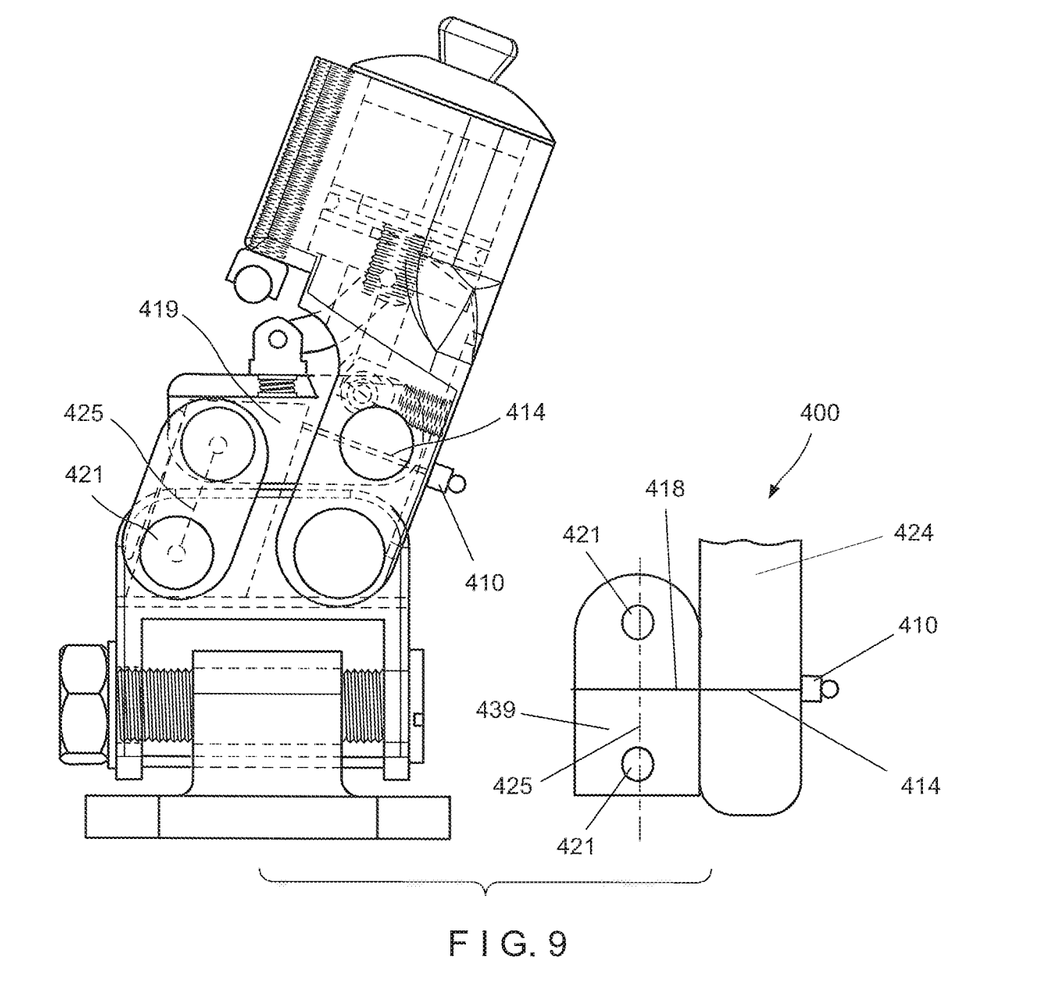
FIG. 9 is a diagram illustrating a lubrication system according to a further embodiment of the invention.

Referring now to FIG. 9 illustrating a further embodiment of the invention. To assure proper operation, a prosthetic ankle joint needs to be lubricated on regular basis. In the prior art to achieve proper lubrication, it is typically necessary to disassemble the unit causing substantial hardship to the patient and also causing a great deal of inconvenience to the practitioners in the field of prosthetic devices. This labor-intensive lubrication process has been significantly simplified by the lubrication system 400 of the invention. A lubricant fitting 410 is mounted on the posterior aspect of the lower depending arm 424 of the torque bracket and is formed with a nipple connection associated with application of a lubricant dispenser or a lubricant gun. The lubricant fitting 410 consists of an outer body which houses a retaining spring applying a pressure to a ball. The ball is arranged for motion within the outer body. A pressured lubricant applied by the dispenser forces the ball to move inwardly in the body of fitting 410 against the forces of the retaining spring, allowing the lubricant to pass into a channel 414 formed in the lower depending arm 224. The lubricant fitting 410 functions as a valve that opens under pressure to allow lubricant to pass through the channel 414 and to be forced into the system. When application of pressurized lubricant ceases, the spring action returns the ball to its initial position to close the fitting 410. Movement of the ball within the fitting 410 excludes dirt penetration into the system and functions as a check valve to prevent lubricant to escape from the fitting. FIG. 9 shows a resilient block or a bumper 419, which is provided to achieve active dorsiflexion. Upon deformation, the resilient block slowly returns to its original shape, and to bring the ankle joint back to its original resting point. By slowly returning to its original shape the resilient block provides a few degrees of dorsiflexion to enable ground clearings during swing phase. The bumper 419 is formed with two axels 421 interconnected by a passage 425 and a longitudinal channel 418 allowing the lubricant to pass through.

When the torque clamp is in the upright or the neutral position, as illustrated on the right side of FIG. 9, the lubricant fitting 410 is in contact with the channel 414 which passes through a lower depending arm 424 and come into a contact with the posterior region of the bumper 419. In the illustrated position the channel 414 is connected to the longitudinal channel 418 of the bumper. Thus, as the lubricant is injected through the fitting 410 it passes through the channel 414 and translates the channel 418 initiated in the posterior area of the bumper. In the lubrication system of the invention lubricant passes between the front portion of the lower depending arm 424 and a rear portion of the bumper 419. Than the lubricant is transported to the front edge of the bumper and it also translates to the passage 425 passing through axel area of the bumper lubricating both the axels and the area between the bumper and the base and the top portion area between the bumper and horizontal or top leg. Therefore, with one lubrication step all areas of the device are simultaneously lubricated. This adequately assures required lubrication and smooth operation of the unit with periodic greasing through the lubricant fitting.

What is claimed is:

1. A prosthetic ankle joint having a dorsiflexion mechanism for achieving active dorsiflexion between a foot and a leg and formed with first and second active dorsiflexion assemblies, said prosthetic ankle joint including a torque bracket pivotably connected to a base assembly by a linkage assembly, the torque bracket having an upper arm, a lower arm extending downwardly from the upper arm, the linkage assembly having a top portion and two spaced from each other side walls extending from the top portion, the dorsiflexion mechanism is disposed at an interface between an interior of the torque bracket, the lower arm and the linkage assembly, wherein said prosthetic ankle joint comprises, an adjustment pin comprising an inner portion and an outer portion, the first and second active dorsiflexion assemblies separated by the adjustment pin, each said dorsiflexion assembly comprises a channel oriented transversely to the adjustment pin, each said channel houses an inner active dorsiflexion adjustment ball engaging the inner portion of the pin, an outer ball engaging a respective detent formed in the respective side wall and an adjustment biasing element provided to engage the respective inner ball and the outer ball.

2. A prosthetic ankle joint of claim 1, wherein the inner portion of the adjustment pin is formed having a conical configuration and the outer portion is formed with threads adapted for engagement with threads of an aperture.

3. A prosthetic ankle joint of claim 2, wherein as the pin is rotated in one direction it is adjusted inwardly, so that the inner conical portion exerts pressure on the inner balls resulted in the outer balls to be disposed within the detents in the side walls.

4. A prosthetic ankle joint of claim 3, wherein as a patient placed into a position loading a toe, pressure exerted by the inner conical portion of the pin is applied on the inner balls pushing the biasing elements and pushing the outer balls to allow the outer balls to migrate into the detents to assure that a dorsiflexed relationship exists between the foot and the leg and to assure up position of the toe.

5. A prosthetic ankle joint of claim 3, wherein a fixed position is maintained when the foot is in a dorsiflexed position allowing a momentary stationary position, wherein toes are pointed upward in a swing phase.

6. A prosthetic ankle joint of claim 2, wherein as the adjustment pin is turned in one direction and pressure is applied on the inner adjustment balls to increase pressure on the biasing elements and to increases the pressure on the outer balls, the outer balls engage the respective detents, while the foot remains in dorsiflexed position.

7. A prosthetic ankle joint of claim 6, wherein when a gait cycle is advanced through swing phase and a dorsiflexion angle in relation to the leg is increased and toe up position is provided, so that when said phase of the gait cycle is complete and the patient then goes into heel strike, force of heel strike overcomes tension of the biasing elements forcing the outer balls into the detents allowing the ankle to release its captive state holding the foot in upright position.

8. A prosthetic ankle joint of claim 2, wherein said biasing element is a spring.

* * * * *